United States Patent [19]

Enders

[11] 4,301,142
[45] Nov. 17, 1981

[54] METHOD AND REAGENT FOR THE DETECTION OF INFECTIOUS MONONUCLEOSIS AND PREPARATION THEREOF

[75] Inventor: Burkhard Enders, Marburg an der Lahn, Fed. Rep. of Germany

[73] Assignee: Behringwerke Aktiengesellschaft, Marburg/Lahn, Fed. Rep. of Germany

[21] Appl. No.: 90,258

[22] Filed: Nov. 1, 1979

[30] Foreign Application Priority Data

Nov. 4, 1978 [DE] Fed. Rep. of Germany ....... 2847877

[51] Int. Cl.³ .................... G01N 33/54; G01N 33/58
[52] U.S. Cl. .................................. 424/8; 23/230 B; 252/408; 424/3; 424/7; 424/12
[58] Field of Search ............................. 424/3, 7, 8, 12; 23/230 B; 252/408

[56] References Cited

U.S. PATENT DOCUMENTS

| | | | |
|---|---|---|---|
| 3,426,123 | 2/1969 | Hoff | 424/12 |
| 3,553,310 | 1/1971 | Csizmas | 424/12 X |
| 4,157,383 | 6/1979 | Sedlacek | 424/3 |

OTHER PUBLICATIONS

Becht, The J. of Immunol., vol. 101, 1968 pp. 18–22.

Primary Examiner—Anna P. Fagelson
Attorney, Agent, or Firm—Curtis, Morris & Safford

[57] ABSTRACT

What is disclosed are a reagent for the detection of infectious mononucleosis by agglutination and a process for its manufacture.

6 Claims, No Drawings

METHOD AND REAGENT FOR THE DETECTION OF INFECTIOUS MONONUCLEOSIS AND PREPARATION THEREOF

This invention relates to a reagent for the detection of infectious mononucleosis, above all in body fluids, by agglutination, and to a process for the preparation of said reagent.

Infectious mononucleosis (IM) or Pfeiffer's disease is a feverish disease observed in children and young adults. The cause is not yet precisely known. It can be assumed that the Epstein-Barr virus (EBV) is the etiological agent. It is known that during the course of the infection up to 80% of the patients produce heterophilic antibodies and, hence, the detection thereof is of diagnostic value. Heterophilic antibodies have the property of aggutinating sheep erythrocytes, but in many cases this agglutination is disturbed by antibodies which are not characteristic of mononucleosis. Therefore, it has been necessary to carry out relatively complicated and time-consuming test series to identify and differentiate the IM specific, heterophilic antibodies (so-called differential adsorption tests).

It has already been described that the specificity of the test for infectious mononucleosis can be improved by using horse erythrocytes instead of sheep erythrocytes, but this process has not been satisfactory either. DE-PS No. 1,598,928 describes a reagent for the detection of infectious mononucleosis. According to this patent horse erythrocytes are treated with aldehydes and stabilized. As compared to earlier methods, this constitutes progress with respect to the specificity and methodology of the test system, but it is not possible either to recognize therewith all sera of carriers of IM specific heterophilic antibodies as such.

Hence, it is still desirable to provide a highly specific and an extremely sensitive test system for the detection of mononucleosis.

It has now been found that a treatment of animal erythrocytes, chiefly wether and horse erythrocytes, with sulfosalicylic acid yields a specific agglutinating reagent for the detection of IM antibodies.

The present invention, therefore, provides a reagent for the detection of heterophilic antibodies of infectious mononucleosis in body fluids by agglutination, said reagent containing erythrocytes of mammals, especially of wethers or equidae, chiefly horses, which have been treated with sulfosalicylic acid and optionally colored with a dyestuff.

The treatment of erythrocytes with sulfosalicylic acid has been described by H. Becht in J. Immunol. 1968, pages 18 to 22. Erythrocytes which have been treated in the manner described in this publication are less suitable as a test reagent for infectious mononucleosis than those treated with a higher concentration of sulfosalicylic acid.

According to the present invention, the erythrocytes, preferably erythrocytes of wether or horse, are treated with aqueous, 2 to 10%, preferably 2.5% (g/v) sulfosalicylic acid, preferably 5-sulfosalicylic acid, until the color of the erythrocytes turns from red to brown. To this end, about equal parts by volume of a dense erythrocyte suspension of 5 to 20% (w/v) of erythrocytes in water or a suitable buffer solution and sulfosalicylic acid solution are blended. Buffering of the erythrocyte suspension and the addition of physiologically acceptable suspension-stabilizing substances, mainly suitable polymers such as polyvinylpyrrolidone or dextran, known to the expert for the stabilization of erythrocyte suspensions, proved to be advantageous.

After the treatment of the erythrocytes with sulfosalicylic acid, which is continued until the color of the suspension has turned from red or brown, generally after a few minutes only, the erythrocytes are separated by sedimentation or centrifugation, repeatedly washed with an isotonic, preferably buffered, salt solution. After this treatment the reagent is, in principle, ready for use. For the detection of IM the erythrocyte suspension is adjusted to a cell density of 5 to $20 \times 10^8$/ml.

For storage it proved to be suitable to add stabilizing additives to the suspension, as is generally known for reagents containing treated erythrocytes. Neutral salts normally employed in biochemistry are used, mainly sodium chloride, buffer mixtures, preferably citrates and citric acid, carbohydrates such as dextrose, or also nucleotides such as inosine, adenine and guanosine, and antimicrobial substances such as chloroamphenicol or neomycin. The suspension should not have an extreme pH value, but is suitably kept around the neutral point; pH values in the range of from 7.0 to 7.5 proved to be especially suitable.

Erythrocytes that have been treated with an aldehyde or with sulfosalicylic acid loose the brightness of color of the native erythrocytes. To improve the readability and thus the degree of detection of heterophilic IM antibodies, it is a further object of the present invention to color the erythrocytes treated with sulfosalicylic acid. Suitable dyestuffs are those hitherto used by the expert for coloring erythrocytes and known in serology, histology and bacteriology. Especially suitable dyestuffs are basic dyestuffs of the triarylamine, triarylmethane and methine series such as crystal violet, malachite green, fuchsin; acid and basic azo dyestuffs such as trypan blue and Ponceau red; phthaleins such as eosin and rhodamines; moreover Coomassie ® blue and the dyestuffs as used in the numerous modifications of coloring microscopic preparations according to Ziehl and Neelsen, just to mention a few of them.

The test results are especially easy to read when the reagent according to the invention is colored with a blue dyestuff, for example Coomassie blue (Anazolenum natricum).

The erythrocytes treated according to the invention are colored with one of the aforesaid dyestuffs mentioned by way of example by methods known from serology. The erythrocyte suspension is combined with the dyestuff solution in a usual concentration and the course of coloring is observed. As soon as the color intensity appears to be sufficient, the erythrocytes are separated from the dyestuff solution by sedimentation or centrifugation, the erythrocytes are repeatedly washed as described above, stabilizers are added and then they are suspended again to give a suspension containing from 5 to $20 \times 10^8$ erythrocytes per milliliter.

The reagent containing the colored or the uncolored erythrocytes is suitably stored at a temperature below room temperature but above 0° C., preferably at about +3° to +6° C.

To carry out the diagnostic process for the detection of IM antibodies a constant amount of erythrocytes treated in accordance with the invention is added in a dilution series to the serum suspicious of heterophilic antibodies and the agglutination, if any, is evaluated. The agglutination is preferably carried out on glass slides or larger plates subdivided into individual compartments. The test can also be carried out in an especially advantageous manner on a known spot plate. The agglutination of the colored erythrocytes is very easy to observe and the evaluation of the agglutination is much better then with erythrocytes that have not been colored.

The test for the detection of IM is positive when a macroscopically visible coarse agglutination, a socalled plaque formation, becomes visible. In doubtful cases. The use of a magnifying glass or a plate microscope facilitates the recognition of the agglutination. The test is negative when the suspension of the test erythrocytes remains homogeneous and shows fine grains.

The following example illustrates the invention.

EXAMPLE

(A) Treatment of horse erythrocytes 350 ml of fresh horse blood in Alsever's solution (1:1) are centrifuged and washed five times, each time for 10 minutes in 10 times the amount, calculated on the volume of the erythrocyte sediment, of phosphate-buffered sodium chloride solution (PBS) of pH 7.2. Centrifugation is carried out at 3000 revolutions per minute. In the meantime 15 g of polyvinylpyrrolidone (PVP, molecular weight 350,000) are dissolved in 1.500 ml of phosphate buffered NaCl solution (PBS, pH 7.2). After the last washing of the erythrocytes, the sediment is adjusted to give a 5 to 10% erythrocyte suspension by adding the 1% PVP-PBS solution.

The same volume of a 2.5% 5-sulfosalicylic acid solution in 1% PVP solution is then added dropwise while stirring (magnetic stirrer) to the erythrocyte suspension and the whole is allowed to react for 30 to 40 minutes at room temperature. The color turns from red to brown directly after the complete addition of the sulfosalicylic acid-PVP-PBS solution. 30 minutes after the discoloration of the erythrocyte suspension, the erythrocytes are washed 5 times in PBS of pH 7.2 and separated by centrifugation (20 minutes at 3000 rpm for each washing).

(B) Coloration of the erythrocytes treated with sulfosalicylic acid

For the preparation of a red colored cell suspension, Ziehl-Neelsen's carbolfuchsin solution (ZN-solution Merck 9215) is used. The sulfosalicylic acid-treated erythrocytes are colored after the second wash of the erythrocyte sediment as described sub (A). The sediment is taken up in a ZN-solution prepared by diluting the commercialized ZN solution in a ratio 1:30 with PBS, pH 7.2, and the whole is maintained for 15 minutes at room temperature. Thereafter, the sediment is again washed three times with PBS of pH 7.2 as described sub (A). The supernatant of the last wash is water-clear. A 10% red erythrocyte suspension is prepared by adding a stabilizer solution as described sub (C). The suspension is kept in a refrigerator until it is further processed.

(C) Preparation of the stabilizer solution of pH 7.2

The following substances are dissolved in 1,000 ml of distilled water:

20.5 g of anhydrous dextrose
8.0 g of sodium citrate . 3 H$_2$O
4.2 g of NaCl
0.55 g of citric acid
0.429 g of chloroamphenicol
0.122 g of neomycin hydrochloride (832 mg of neomycin B-base per g)
4.0 g of inosine
0.2 g of adenine
0.2 g of guanosine and
0.1 g of thimerosal The solution obtained is adjusted to pH 7.3 by means of 5 N NaOH and then filtered under sterile conditions.

(D) Preparation of the IM reagent

For use in the IM reagent on glass slides or glass agglutination plates, a 7% erythrocyte suspension in stabilizer solution (C) is prepared. The same cell concentration is valid for uncolored as well as colored erythrocytes.

When using spot plates of porcelain, a 3.5% cell concentration in stabilizer solution (C) gives optimal results. The agglutination of colored erythrocytes is more distinct and, therefore, the reaction is easier to detect. The reagent is filled into small bottles with screw caps with a drop pipette having a drop volume of about 35 μl. The reagent is kept at a temperature of from +4° to +6° C.

(E) Carrying out of IM test

One drop of the serum of a patient (35 μl) is dropped by means of the pipette in the center of a compartment of a test plate and cautiously mixed by a clean rod with one drop of the above IM reagent (D). Thereafter, the test plate is slightly rotated for about 2 minutes.

A positive result of infectious mononucleosis is found if a macroscopically coarse agglutination (plaque formation on the border) becomes visible. In case of doubt a magnifying glass or a plate microscope can be used.

A negative result is characterized by the absence of an agglutination pattern. In this case, the suspension remains homogeneous with fine grains.

In 107 patients suffering from infectious mononucleosis 88.8% of the tests with the reagent according to the invention were positive.

What is claimed is:

1. A method for testing for the presence of antibodies of infectious mononucleosis in a body fluid, which method comprises combining the body fluid to be tested with horse erythrocytes which have been treated with sulfosalicylic acid in an amount sufficient such that the color of the erythrocytes turns from red to brown, and observing for agglutination indicating the presence of said antibodies.

2. A method as in claim 1 wherein said horse erythrocytes have been colored with a dyestuff.

3. A method for making a reagent for testing for the presence of antibodies of infectious mononucleosis in a body fluid which comprises adding a 2% to 10% aqueous solution of sulfosalicylic acid to a 5% to 10% aqueous suspension of horse erythrocytes in an amount such that the color of the erythrocytes turns from red to brown, washing and recovering the treated erythrocytes, and suspending them in a stabilizing solution.

4. A method as in claim 3 wherein said erythrocytes are colored with a dyestuff after treatment with sulfosalicylic acid and prior to suspension in the stabilizing solution.

5. A reagent prepared by the method of claim 3 for testing for the presence of antibodies of infectious mononucleosis in a body fluid.

6. A reagent as in claim 5 wherein said horse erythrocytes have been colored with a dyestuff.

* * * * *